United States Patent [19]

Tuli et al.

[11] Patent Number: 5,714,661
[45] Date of Patent: Feb. 3, 1998

[54] PROCESS FOR THE PREPARATION OF SYNTHETIC LUBRICANT BASE STOCKS

[76] Inventors: Deepak Kumar Tuli, 866 Sector-9, Faridabad-121006; Sabyasachi Sinha Ray, 65, Pocket B, Sarita Vihar, New Delhi 110044, both of India; Rakesh Sarin, 2204, Sector-9, Faridabad, Haryana, India, 121006; Madan Mohan Rai, 886, Sector-15; Sobhan Ghosh, 188, Sector-14, both of Faridabad, India, 121007; Akhilesh Kumar Bhatnagar, 205, Sector-7A, Faridabad, Haryana, India, 121006

[21] Appl. No.: 655,925

[22] Filed: May 31, 1996

[51] Int. Cl.$^6$ ................................ C07C 2/10; C07C 2/74
[52] U.S. Cl. .................. 585/533; 585/255; 585/326; 585/329; 585/324; 585/330; 585/520
[58] Field of Search .................. 585/255, 326, 585/329, 533, 324, 330, 520

[56] References Cited

U.S. PATENT DOCUMENTS

| | | | |
|---|---|---|---|
| 4,172,855 | 10/1979 | Shubkin et al. | 585/10 |
| 4,400,565 | 8/1983 | Darden et al. | 585/10 |
| 4,417,088 | 11/1983 | Miller | 585/533 |
| 4,420,646 | 12/1983 | Darden et al. | 585/10 |
| 4,420,647 | 12/1983 | Hammond et al. | 585/10 |
| 4,430,516 | 2/1984 | La Pierre et al. | 585/533 |
| 4,434,308 | 2/1984 | Larkin et al. | 585/10 |
| 4,902,847 | 2/1990 | Juguin et al. | 585/533 |
| 5,026,933 | 6/1991 | Blain et al. | 585/7 |
| 5,068,487 | 11/1991 | Theriot | 585/510 |
| 5,105,051 | 4/1992 | Pelrine et al. | 585/528 |
| 5,108,970 | 4/1992 | Young et al. | 502/74 |
| 5,120,891 | 6/1992 | Sanderson et al. | 585/533 |
| 5,134,242 | 7/1992 | Le et al. | 585/533 |
| 5,171,909 | 12/1992 | Sanderson et al. | 585/255 |
| 5,191,139 | 3/1993 | Sanderson et al. | 585/520 |
| 5,191,140 | 3/1993 | Akatsu et al. | 585/525 |

*Primary Examiner*—Glenn Caldarola
*Assistant Examiner*—Thuan D. Dang
*Attorney, Agent, or Firm*—Spencer & Frank

[57] ABSTRACT

A process for the preparation of oligomers which are used in synthetic lubricant base stocks. The oligomers are prepared by contacting a mixture of linear olefins and n-paraffins contained in cracked refinery streams having 6 to 24 carbon atoms with activated Y-zeolites. The oligomers and unreacted monomers are subjected to the step of hydrogenation and the lower saturated paraffins are separated therefrom to produce synthetic lubricant base stock.

16 Claims, 1 Drawing Sheet

5,714,661

PROCESS FOR THE PREPARATION OF SYNTHETIC LUBRICANT BASE STOCKS

FIELD OF INVENTION

This invention relates to the preparation of synthetic lubricant base stocks, and more particularly to synthetic lubricant base stocks made by oligomerizing the alph-olefins contained in cracked refinery distillates rich in alpha olefins having 6 to 24 carbon atoms. These synthetic lubricant base stocks are prepared by oligomerising linear olefins of cracked refinery distillates using a catalyst comprising steam activated Y-zeolites.

BACKGROUND OF THE INVENTION

Performance of synthetic oligomeric hydrocarbon fluids is much superior to natural mineral oils, when used as lubricating oil base stock. This superiority in terms of appropriate viscosity over a wider temperature range, low pour points, higher oxidative and thermal stability has led to the development of polyalpha-olefins (PAO) synthetic lubricants. These synthetic lubricants exhibit lower friction characteristics and are used in various types of equipment, including auto engine, transmission, worm gears and traction devices.

Synthetic PAO type base stocks may be prepared by oligomerising alapha-olefin monomers to form oligomers, mainly dimer trimer, tetramer and small amount of higher oligomers. These oligomers are further hydrogenated to improve their oxidative stability to obtain fluids which can be used as synthetic lubricant base stocks.

Synthetic base stocks are produced in a broad range of viscosity grades. It is common practice to classify the base stocks by their viscosities, measured in centistockes (cSt) at 100 deg C. Those base stocks with viscosities less than or equal to about 4 cSt are commonly referred to as "low viscosity" base stocks, whereas base stocks having a viscosity in the range of around 40 to 100 cSt are commonly referred to as "high viscosity" base stocks. Base stocks having a viscosity of about 4 to about 10 cSt are referred to as "medium viscosity" base stocks.

The viscosity of the base stocks is determined by the length of the oligomer molecules formed during the oligomerization reaction. The degree of the oligomerization is affected by the catalyst and reaction conditions employed during the reaction. The length of the carbon chain of the monomer starting material also has a direct influence on the properties of the oligomer products. Fluids prepared from short chain monomers tend to have low pour points and moderately low viscosity indices, whereas fluids prepared from long chain monomers tend to have moderately low pour points and higher viscosity indices. Oligomers prepared from long chain monomers generally are more suitable than those prepared from shorter chain monomers and are used as medium viscosity synthetic lubricants. Furthermore, the branching on the alkyl chain has a significant effect on the pour point and viscosity indices. The effective oligomers for use as lubricant base stocks should have sufficient branching to have low pour points, but not so much branching so as to have poor viscosity indices.

One known approach to oligomerise long chain olefins, generally having 10 carbon atoms, to prepare synthetic lubricant base stocks is to contact the olefin with boron trifluoride together with a promoter at a reaction temperature sufficient to effect oligomerization of the olefin. See, for example, U.S. Pat. Nos. 4,400,565; 4,172,855; 4,420,646; 4,420,647; 4,434,308; 5,068,487 and 5,191,140. However, boron trifluoride is a pulmonary irritant, and breathing the gaseous fumes formed by hydration of the gas with atmospheric moisture poses health hazards. Thus, a method for oligomerizing long chain olefins using a less hazardous catalyst would be an improvement in the art.

Developments in zeolites and their application as catalysts to oligomerise lower olefins to gasoline, jet fuel and diesel has been reported (See U.S. Pat. No. 4,902,847). Many reports have appeared in which long carbon chain olefins have been oligomerised by contacting with acidic clays, zeolites and chemically activated zeolites. The long chain alpha-olefins suitable for oligomerisation are generally made by the thermal cracking of paraffinic hydrocarbons or by the well known zeigler ethylene chain growth and displacement process using triethylaluminium.

Texaco discovered that it is possible to prepare synthetic lubricant base stocks in good yield by oligomerising long chain olefins using certain acidic montmorillonite clay catalysts (See U.S. Pat. No. 5,171,909). Texaco chemical company also discovered that synthetic lubricant base stocks can be prepared by oligomerizing linear olefins using a sulfate activated Group IV oxide, particulary zirconium dioxide (See U.S. Pat. No. 5,191,139). An improved process is also disclosed by Texaco for preparing synthetic lubricant base stocks by oligomerising linear olefins using a catalyst comprising a super-dealuminated y-zeolite (See U.S. Pat. No. 5,120,891). Mobil Oil Corporation has developed a process for oligomerizing alpha-olefins to produce olefin oligomers useful as lubricants and lubricants additives using a catalyst comprising a supported reduced group VIB metal, preferably chromium, in the form of its oxide (See U.S. Pat. No. 5,105,051). Exxon Chemical Patents have disclosed catalysts and process for oligomerization of olefins by nickel containing zeolite catalyst, the zeolite being a Cs or Ba exchanged CSZ-1, high silica utrastable faujasite and zeolites iso-structural with mazzite (See U.S. Pat. No. 5,108, 970). Intermediate pore size silicaceous crystalline molecular sieves were used to oligomerise olefins at elevated temperature with lower hydrogen transfer activity (See U.S. Pat. No. 4,417,088). A patent assigned to Mobil Oil Corporation (U.S. Pat. No. 4,430,516) describes the conversion of lower olefins to C10+ distillate range by use of large pore crystalline aluminosilicate zeolite catalysts at elevated temperatures and pressures.

However, all these processes pertain to oligomerazation of either pure or mixtures of pure alpha-olefins, and suprisingly there are no reports on the utilization of liniear olefins contained in refinery streams, for the production of synthetic lubricant base stocks. Various refinery produced cracked distillate streams, particularly, from Coker and FCC units, are quite rich in desired alpha-olefins, which can be selectively concentrated by the process of urea adduction. Applicants have discovered that a conversion of long chain olefins to oligomer may be effected by contacting the paraffins/olefins petroleum fraction, obtained from the cracked refinery distillate stream through urea adduction process, with a catalyst comprising a Y-zeolite. The extent of oligomerisation of these olefins could be appreciably enhanced when the Y-zeolites had higher silica/alumina ratio, i.e., super-dealuminated ultrastable Y-zeolites. Applicants have furthermore discovered, surprisingly, that a higher conversion of these olefins contained in cracked refinery stream distillates may be obtained by contacting with Y-zeolites, which have been steam activated prior to use. This steam activation of Y-zeolites makes the catalysts to be more active and produce a higher olefin conversion. Additionally, catalysts treated with steam remained active during the oligomerisation reaction for a longer period of time. In addition to being excellent catalysts, these Y-zeolites and super-dealuminated ultrastable Y-zeolites are relatively safe and more easily handled than boron trifluoride. These steam activated catalysts also provide synthetic lubricant base stocks which have a high dimer/trimer ratio, which is desirable characteristics for some applications.

OBJECTS OF THE INVENTION

An object of the present invention is to propose an improved process for oligomerising olefins of refinery streams contained in cracked refinery distillates rich in alpha olefins having 2 to 24 carbon atoms by using a catalyst comprising stream activated Y-zeolites.

A further object of this invention is to propose a process for oligomerising olefins of refinery streams having a higher conversion.

Yet another object of the present invention is to propose a process for producing PAO type synthetic lubricants, by utilising linear olefins obtained from cracked refinery distillate streams having a higher conversion than compared to x-zeolites of the prior art.

DESCRIPTION OF INVENTION

The invention relates to a process for the preparation of oligomers of olefins contained in the olefin:paraffin mixtures obtained from the cracked refinery distillates. The olefin:paraffin mixture containing 6 is to 25 carbon atoms is contacted with steam activated Y-zeolites at elevated temperature. In the instance of lubricating oil base stocks, such a step is followed by catalytic hydrogenation and vacuum removal of lower saturates to obtain olefin oligomers suitable for use as lubricating oil base stocks.

The olefins oligomerised by the process of present invention are of petroleum origin and comprising of both internal and terminal olefins. Thermal cracking and catalytic cracking of the heavy feed stock like that of atmospheric/vacuum distillation residue is routinely carried out in the petroleum refining industry. This activity is associated with conversion by cracking of long chain residual hydrocarbon to obtain more of distillates fuels. However, thermal and catalytic cracking is generally associated with dehydrogenation to produce olefinic components which are present in distillate fuels. Depending upon the serverity of thermal or catalytic operation, these olefinic hydrocarbons are found in the range of 20–40% of the distillate fuel composition. Analytical investigations of fuels obtained by these secondary cracking processes indicate that predominately (70–90%) these olefinic compounds are alpha-olefins while the rest are the internal olefins.

Though the refinery distillate fuels from the secondary refining processes like Coker & FCC contain appreciable amounts of aromatics, paraffins, olefins, naphthenes and isoparaffins, several procedures have been reported in literature to selectively separate the mixture of normal paraffins and linear olefins from these distillate fuels. Methods are generally known in the art to obtain linear olefin and linear paraffin mixtures, which contained 20–45% linear olefins, by urea adduction of cracked refinery distillate streams, viz., naphtha, kerosene, diesel and gas oil. See, for example, A. Hoope in "Advances in Petroleum Chemistry and Refining", Vol.8, Ed., Kobe-McKetta, Interscience Publication: New York, 1964, which is incorporated by reference.

The olefins feed stock used in the present invention comprises of the chemical compound having the the general formula: $R\text{---}CH\!=\!\!CH_2$, where R is linear alkyl radical of C4 to C22 carbon atoms, and internal olefins having the formula: $R_1\text{---}CH\!=\!CH\text{---}R_2$ where $R_1$ and $R_2$ may be same or different alkyl radicals of C1 to C23 carbon atoms, provided that the total number of carbon atoms in any one olefin shall be in the range of 6 to 24, inclusive. A preferred range of total number of carbon atoms in any one of the olefin molecule is 10 to 24 with an especially preferred range of 14 to 20. For producing a synthetic lubricant with lower knock values and moderate viscosities the range of carbon atoms in any one olefin should be 16 to 20. However, it was found that the amount of internal olefins in the olefin:paraffin mixture did not have a very significant effect on the characteristics of the polyalpha-olefin type synthetic lubricant obtained after oligomerisation. Thus polyapha-olefin type of synthetic lubricant with good characteristics could be obtained from the olefin:paraffin mixture obtained from the refinery feed stock and having 2–20% of internal olefins provided the total carbon number of the mixture web well within the rate of 6 to 24. As will be apparent from Table 1 reproduced herein below, Be use of a catalyst selected from steam activated Y-zeolite allows the process to be effective with a high conversion efficency from the olefin having the complete range of 6 to 24 carbon atoms.

The oligomerisation feed stock obtained from the cracked refinery distillate streams by the urea adduction process contain a major amount of n-paraffins. These paraffins have the general chemical formula of $R\text{---}CH_2\text{---}R_1$, where R & $R_1$ are the normal chain alkyl radicals which my be same or different but but combined carbon number of R & $R_1$ should be in the range of 5 to 23. Furthermore, these n-paraffins have the same boiling range as that of the linear olefins when obtained from the typical cracked refinery distillate streams by adopting the procedure of urea adduction.

The overall oligomerisation reaction reflects any typical organic reaction involving carbon-cation chemistry, which is well known to those skilled in the art. However, a typical oligomerisation reaction can be represented as

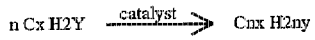

$$n\, C_xH_{2Y} \xrightarrow{\text{catalyst}} C_{nx}H_{2ny}$$

These reactions are sequential in nature i.e. the monomers react to give dimers and which further give the oligomers. However, the reaction parameters and catalyst should be so designed so as to give sufficient opportunity to the initial carbo-cation formed for rearrangement. It has been found experimentally that in absence of such an rearrangements the products formed are of poor pour point and poor viscometrics. A catalyst with proper reaction conditions would lead to oligomeric products that exhibits high viscosity index and low pour points. A perusal of FIG. 1 would explain the rational behind the requirement of carbo-cation isomerisation/rearrangement.

The catalysts used to effect the oligomerisation reaction of olefins of olefin:paraffin feed stock obtained from the cracked refinery distillate streams were Y-zeolites and super dealuminated ultrastable Y-zeolites. These Y-zeolites are distinguished from the X-zeolites on the basis of relative concentration of silicon and aluminium atoms and these have definite effect on the structure/typical properties. The typical Y-zeolite in the hydrated form may be represented by the following formula:

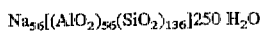

$$Na_{56}[(AlO_2)_{56}(SiO_2)_{136}]250\, H_2O$$

The catalysts useful for the present invention include normal Y-zeolites having silica/alumina ratio of approximately 4.0 to 5.0 and those having high silica to alumin ratio (>10.0). The later category of Y-zeolites can also be called super-dealuminated ultrastable Y-zeolites. These zeolites can be easily obtained by dealuminating a commercial Y-zeolite by treatment with chelating agents like ethylenediamine tetra acetic acid (EDTA), by heat treatment or by hydrothermal treatment. An example of commercial Y-zeolites useful for oligomerisation reaction of the present invention is the Linde LZ-Y-52 and LZ-Y-62. The catalyst LZ-Y-52 contained about 62–64% $SiO_2$ and 22–24 wt% $Al_2O_3$ i.e. $SiO_2/Al_2O_3$ molar ratio of about 4.7 with a pore size of 8 Å, while LZ-Y-62 had $SiO_2/Al_2O_3$ molar ratio of 5.0. The suitable commercially available catalysts of super-dealuminated category include CBV 712, CBV 720, CBV 760 and CBV 780 supplied by PQ Corporation and having a silica to alumina ratio in the range of 10:1 to 80:1. These catalysts which are generally available in powdered form can be easily made in pellets, or extrudates with the help of certain binders, which could be of silica alumina type. These extrudated Y-catalysts had required physical stability and strength necessary for performing the catalytic reactions on a fixed bed reactor. However, for oligomerisation reactions to be done in autoclave (slurry reactor), the commercially available powdered catalysts as such can be used.

The reaction time or catalyst contact period had pronounced effect on the quality of synthetic lubricating oil obtained after oligomerisation. For reaction carried out using catalyst slurry in the feed placed in an autoclave, good results were obtained under autogenous pressure for 0.5 to 8 hrs. with the preferred range of 1–4 hrs.

The temperature at which the oligomerisation can be effected are between 40–350 deg C. with preferred range 120–250 deg C. It has also been noticed in the present invention that heat treatment of catalyst to activate these by partial removal of water is of utmost importance. Complete removal of water by calcination may render these catalysts ineffective. The interlamellar cations present in the zeolites can dissociate the coordinated water molecules making these better proton donars. Thus by careful drying, the acidity of zeolites can be controlled, because these available interlamellar cations can very effectively dissociate the remaining water molecules. Further, the heat treatment can also convert the Bronsted acid centres of the zeolites to the Lewis acid centres. In a preferred embodiment, the catalysts of the present invention, after heat treatment, are activated by steaming at a temperature of 160–220 deg C., with a specially preferred range being 180–200 deg C. This steaming of the catalyst is performed in a reactor tube packed with acatalyst over which superheated steam is passed for 1–4 hrs.

Following the catalytic oligomerisation, the oligomeric polyalpha-olefins still contain one double bond per molecule. Presence of this unsaturation may lead to lower thermal stability of the product. Hence the oligomerised products of the present invention are hydrogenated by following the conventional methods. A number of metallic catalysts are suitable for promoting this hydrogenation reaction and are known to those skilled in the art. These metals include nobel metals like platinum or palladium or transition metals like copper or Raney nickel supported on variety of supports like charcoal, Kieselguhr or alumina.

The unreacted olefinic monomers and the linear paraffins may be removed from the oligomerised products either prior to or after the hydrogenation step. However, since the process of present invention lead to a high conversion of olefins to oligomers, the unreacted olefin and linear paraffin stripping was always carried out after the hydrogenation step. This was done intentionally so as to obtain pure linear paraffins, which have a higher commercial value. Thus, the monomer stripping after hydrogenation was carried out under vacuum using the vacuum distillation procedures known to those skilled in the art. This vacuum distillation was carried out to avoid the use of excessive distillation temperatures which could lead to product breakdown or to avoid the development of colour. The monomer stripped hydrogenated bottoms did not need further purification and were the desired synthetic polyalpha-olefins.

GENERAL PROCEDURE OF OLIGOMERISATION

Figure 1:
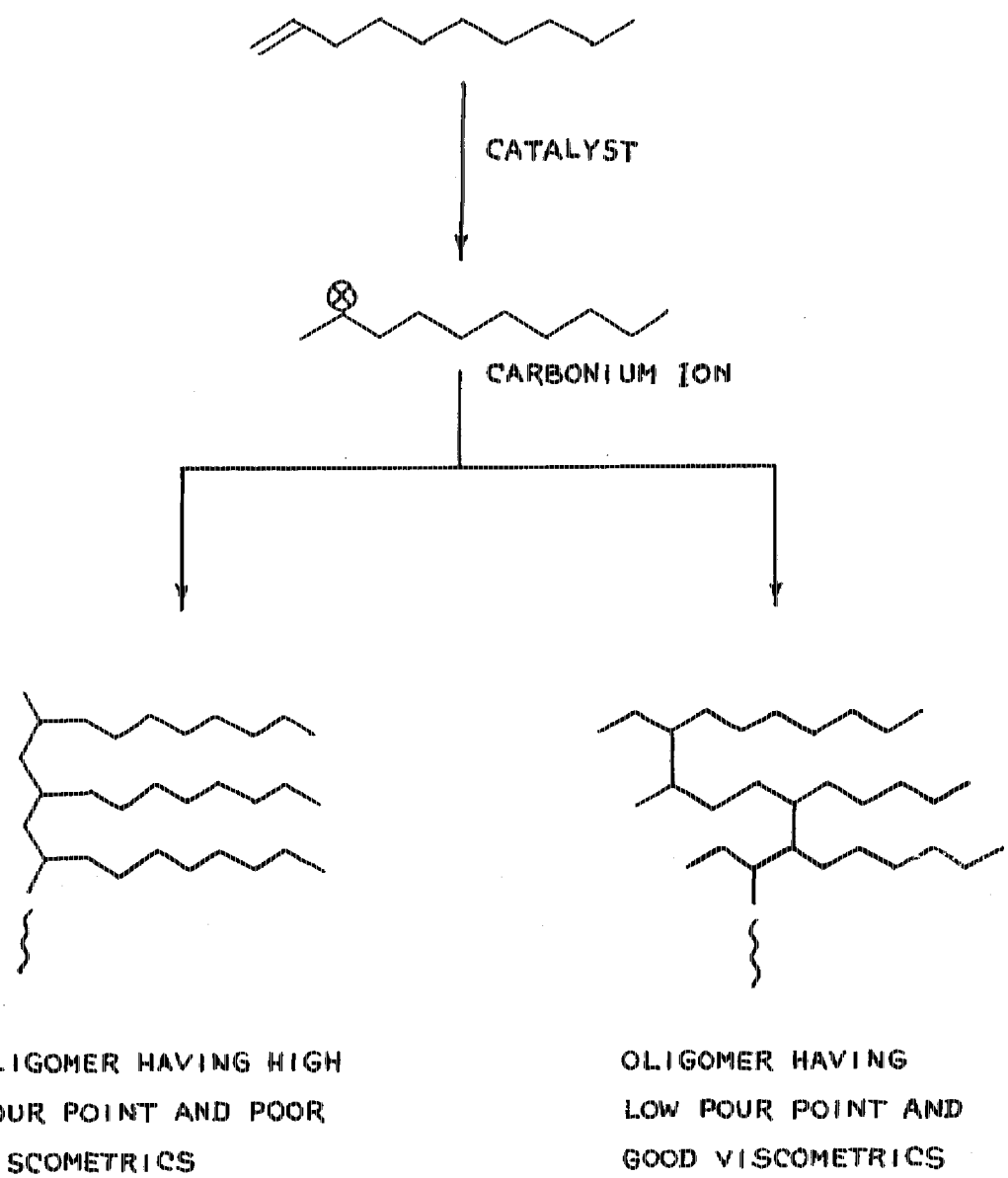
FIG. 1. Figure one represents the oligomerisation reaction and explains the rational behind the requirement of carbocation isomerisation/rearrangement.

Y-zeolites or ultrastable super-dealuminated Y-zeolites were heated at desired temperature for desired time and then activated by passing super-heated steam at desired temperature for desired time. These activated zeolites and the aromatic free, olefin-paraffin petroleum fraction, were then charged into the reactor of the autoclave. The autoclave was flushed with an inert gas, like nitrogen or argon, and contents heated to desired temperature for desired time. After completion of reaction, the catalyst was filtered off and the filtrate was hydrogenated and the paraffins were distilled at reduced pressure to get desired polyalpha-olefins. The product profile as monitored by GC/GPC and visscometric data is presented in Table-1.

TABLE 1

| Ex No. | O:P feed | Catalyst | Steaming temp/time deg C. hrs | Cat % | Reaction temp/time deg C. hrs | Con % | D % | T+ % | D/T+ ratio | Vis* 100 deg cSt |
|---|---|---|---|---|---|---|---|---|---|---|
| 1 | C8–C12 | CBV-720(S) | 180/2 | 7 | 180/3 | 88 | 68 | 20 | 3.4 | 2.57 |
| 2 | C10–C12 | CBV-720(S) | 180/2 | 10 | 160/5 | 85 | 60 | 25 | 2.4 | 2.73 |
| 3 | C12–C14 | CBV-720 | —— | 10 | 160/5 | 56 | 45 | 11 | 4.1 | 2.62 |
| 4 | C13–C15 | CBV-712(S) | 200/1 | 10 | 180/6 | 64 | 50 | 14 | 3.6 | 2.92 |
| 5 | C14–C18 | CBV-760(S) | 200/1 | 12 | 180/6 | 75 | 65 | 10 | 6.5 | 3.99 |
| 6 | C14–C18 | CBV-760(S) | 200/1 | 20 | 160/4 | 78 | 60 | 18 | 3.3 | 4.22 |
| 7 | C16–C20 | CBV-760 | —— | 15 | 180/8 | 56 | 50 | 6 | 8.3 | 3.87 |
| 8 | C16–C20 | CBV-760(S) | 200/1 | 12 | 160/5 | 75 | 60 | 15 | 4.0 | 4.35 |
| 9 | C10–C12 | LZ-Y-52 | —— | 10 | 180/6 | 20 | 14 | 6 | 2.3 | 2.02 |
| 10 | C10–C12 | LZ-Y-52(S) | 180/2 | 10 | 180/6 | 35 | 25 | 10 | 2.5 | 2.49 |
| 11 | C12–C14 | LZ-Y-62(S) | 180/2 | 8 | 180/6 | 59 | 48 | 11 | 4.4 | 2.67 |
| 12 | C8–C10 | CBV-712(S) | 180/2 | 10 | 160/6 | 75 | 52 | 23 | 2.3 | 2.51 |
| 13 | C16–C18 | CBV-760(S) | 200/1 | 6 | 160/4 | 78 | 58 | 20 | 2.9 | 4.21 |

TABLE 1-continued

| Ex No. | O:P feed | Catalyst | Steaming temp/time deg C. hrs | Cat % | Reaction temp/time deg C. hrs | Con % | D % | T+ % | D/T+ ratio | Vis* 100 deg cSt |
|---|---|---|---|---|---|---|---|---|---|---|
| 14 | C19-C22 | CBV-780(S) | 200/1 | 8 | 180/8 | 82 | 64 | 18 | 3.6 | 5.29 |
| 15 | C16-C18 | CBV-780(S) | 200/1 | 10 | 160/5 | 78 | 59 | 19 | 3.1 | 5.02 |
| 16 | C14-C16 | CBV-780 | --- | 12 | 180/6 | 58 | 48 | 10 | 4.8 | 4.28 |
| 17 | C12-C14 | LZ-Y-62 | --- | 8 | 180/6 | 47 | 39 | 8 | 4.9 | 2.56 |

S = Steamed, Con = Conversion, D = Dimer, T+ = Trimer plus higher oligomers, * = Determined after hydrogenation.
CBV 712, 720, 760 & 780 were obtained from PQ Corporation and had silica to alumina ratio of 11.5, 30, 60 & 80 respectively; LZ-Y-52 & LZ-Y-62 are sold by UOP and had silica to alumina ratio of 4.7 & 5.0 respectively.

GENERAL PROCEDURE OF HYDROGENETION

An autoclave was charged with oligomeric reaction product and finely powdered palladium on charcoal hydrogenation catalyst. The autoclave was flushed and then pressurised with hydrogen at 700 psi. The mixture was heated at 180 deg C. for 3 hours. Reaction mixture was then cooled to ambient temperature, catalyst filtered and product distilled to yield colorless synthetic polyalpha-olefin based lubricant.

We claim:

1. A process for the preparation of oligomers comprising subjecting a mixture of linear olefins and n-paraffins containing from 6 to 24 carbon atoms obtained by the step of urea adduction from cracked refinery streams to a catalyst comprising Y-zeolites activated by steam at a temperature between 160°–220° C., said catalyst having a silica to alumina ratio of about 4:1 to 80:1.

2. The process of claim 1 wherein said catalyst has a silica to alumina ratio of about 4:1 to 10:1.

3. The process of claim 1 wherein the Y-zeolite is an ultrastable super-dealuminated Y-zeolite having a silica to alumina ratio of about 10:1 to 80:1.

4. The process of claim 1 wherein the Y-zeolites are activated by a steam treatment of 180°–200° C. prior to contact with the olefin:paraffin mixture for a period of 1 to 4 hours.

5. The process of claim 1 wherein the oligomerisation is carried out at a temperature of 40°–350° C. at autogenous pressure for a period of 0.5 to 8 hours.

6. The process of claim 1 wherein the olefins of the olefin:paraffin mixture contain 1–20 wt % internal olefins.

7. A process for the preparation of synthetic lubricant base stock comprising:

a) subjecting a mixture of linear olefins and n-paraffins containing from 6 to 24 carbon atoms obtained by the step of urea adduction from cracked refinery streams to the step of oligomerization in the presence of a catalyst comprising Y-zeolites activated by steam at a temperature of 160–220° C., said catalyst having a silica to alumina ratio of about 4:1 to 80:1;

b) hydrogenation of the oligomers and unreacted monomers of step (a); and c) separation of lower saturated paraffins to produce synthetic lubricant base stock.

8. The process of claim 7 wherein the Y-zeolites are activated by a steam treatment at about 180–200° C., prior to contact with olefins contained in the olefin:paraffin mixture obtained from the cracked refinery streams.

9. The process of claim 8 wherein the stream activated Y-zeolite has a silica to alumina ratio of 4:1 to 80:1.

10. The process of claim 9 wherein the olefins obtained from the cracked refinery stream contains from 2 to 20 wt. % of internal olefins.

11. The process of claim 8 wherein said steam treatment is carried out for a period of 1–4 hours.

12. The process of claim 9 wherein the oligomerisation is carried out at a temperature of 40°–350° C. at autogenous pressure for a period of 0.5 to 8 hours.

13. The process of claim 5 wherein the oligomerisation is carried out at a temperature of 120° C. to 250° C.

14. The process of claim 5 wherein the oligomerisation is carried out for 1 to 4 hours.

15. The process of claim 12 wherein the oligomerisation is carried out at a temperature of 120° C. to 250° C.

16. The process of claim 12 wherein the oligomerisation is carried out for 1 to 4 hours.

* * * * *